United States Patent
Cross, Jr. et al.

(10) Patent No.: US 7,725,198 B2
(45) Date of Patent: May 25, 2010

(54) IMPLANTABLE MEDICAL LEAD ASSEMBLIES WITH DELIVERY TETHER

(75) Inventors: Thomas E. Cross, Jr., St. Francis, MN (US); Michaelene M. Williams, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 589 days.

(21) Appl. No.: 11/742,454

(22) Filed: Apr. 30, 2007

(65) Prior Publication Data

US 2008/0269861 A1 Oct. 30, 2008

(51) Int. Cl.
*A61N 1/05* (2006.01)
(52) U.S. Cl. ..................... 607/132
(58) Field of Classification Search ......... 607/115–119, 607/122–133; 606/108, 129, 139, 142–144, 606/148, 222–227
See application file for complete search history.

(56) References Cited

U.S. PATENT DOCUMENTS

| | | | |
|---|---|---|---|
| 4,154,247 | A | 5/1979 | O'Neill |
| 4,289,144 | A | 9/1981 | Gilman |
| 4,458,677 | A | 7/1984 | McCorkle, Jr. |
| 5,086,787 | A | 2/1992 | Grandjean et al. |
| 5,628,779 | A | 5/1997 | Bornzin et al. |
| 5,772,693 | A | 6/1998 | Brownlee |
| 5,967,977 | A | 10/1999 | Mullis et al. |
| 6,066,165 | A | 5/2000 | Racz |
| 6,434,431 | B1 | 8/2002 | Camps et al. |
| 6,574,512 | B1 | 6/2003 | Zhang et al. |
| 6,587,733 | B1 | 7/2003 | Cross, Jr. et al. |
| 6,843,870 | B1 | 1/2005 | Bluger |
| 2002/0116042 | A1 | 8/2002 | Boling |
| 2003/0028232 | A1* | 2/2003 | Camps et al. ............ 607/122 |
| 2005/0016657 | A1 | 1/2005 | Bluger |
| 2005/0033394 | A1 | 2/2005 | Seifert et al. |
| 2005/0203599 | A1 | 9/2005 | Garabedian et al. |
| 2006/0032657 | A1 | 2/2006 | Zarembo |
| 2007/0282410 | A1 | 12/2007 | Cross, Jr. et al. |
| 2008/0039917 | A1 | 2/2008 | Cross, Jr. et al. |
| 2008/0046058 | A1 | 2/2008 | Cross, Jr. et al. |

(Continued)

FOREIGN PATENT DOCUMENTS

EP 0 057 448 A1 8/1982

(Continued)

OTHER PUBLICATIONS

PCT Search Report mailed Oct. 29, 2007; 15 pgs.

(Continued)

*Primary Examiner*—Carl H Layno
*Assistant Examiner*—Jessica Sarcione

(57) ABSTRACT

Implantable lead assembly including a lead body, an elongated conductor, a coiled electrode, and a tether line. The lead body maintains the conductor. The electrode is coupled to the conductor, defining proximal and distal ends. The tether line defines a trailing segment and a leading segment terminating in a leading end. The tether line is coupled to the coiled electrode at a point proximal the distal end, and the leading end extends distal the distal end. With this configuration, a pulling force applied to the leading segment is transferred to the electrode at a point proximal the distal end as a pushing force, thereby minimizing an opportunity for overt stretching of the coiled electrode during implantation. The lead assembly can further include a needle connected to the tether line.

27 Claims, 6 Drawing Sheets

U.S. PATENT DOCUMENTS

| | | |
|---|---|---|
| 2008/0051861 A1 | 2/2008 | Cross, Jr. et al. |
| 2008/0269837 A1 | 10/2008 | Ludlow et al. |
| 2008/0269856 A1 | 10/2008 | Cross, Jr. et al. |
| 2008/0269857 A1 | 10/2008 | Cross, Jr. et al. |
| 2008/0269858 A1 | 10/2008 | Cross, Jr. et al. |
| 2008/0269859 A1 | 10/2008 | Cross, Jr. et al. |
| 2008/0269860 A1 | 10/2008 | Cross, Jr. et al. |

FOREIGN PATENT DOCUMENTS

| | | |
|---|---|---|
| EP | 0 657 185 A2 | 12/1994 |
| WO | 99/30772 | 6/1999 |
| WO | 2004/035133 | 4/2004 |

OTHER PUBLICATIONS

PCT Search Report (mailed Nov. 6, 2007); 11 pgs.
PCT Search Report mailed Nov. 14, 2007; 8 pgs.
PCT Search Report (mailed Jan. 3, 2008); 6 pgs.
PCT Search Report mailed Feb. 4, 2008; 8 pgs.

* cited by examiner

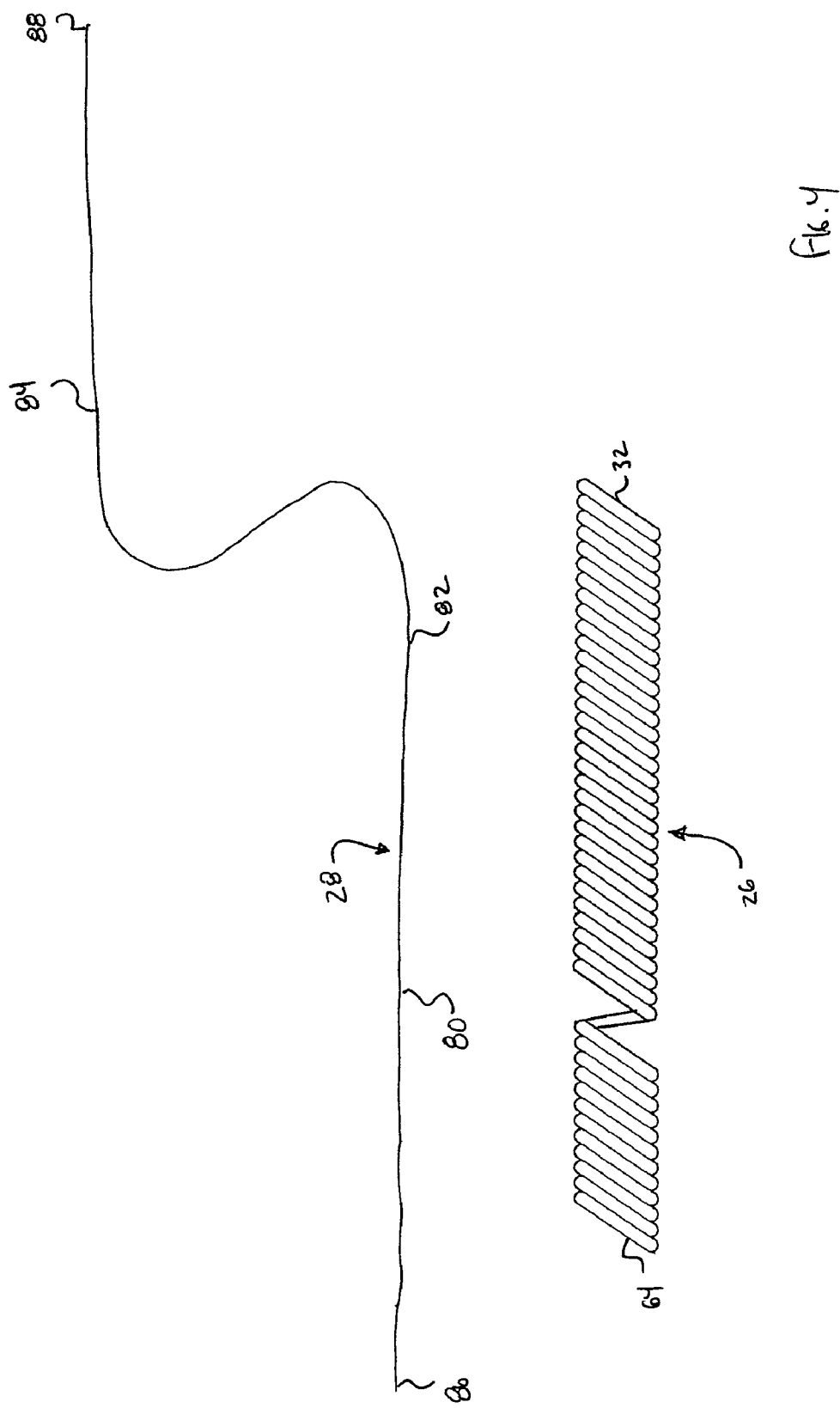

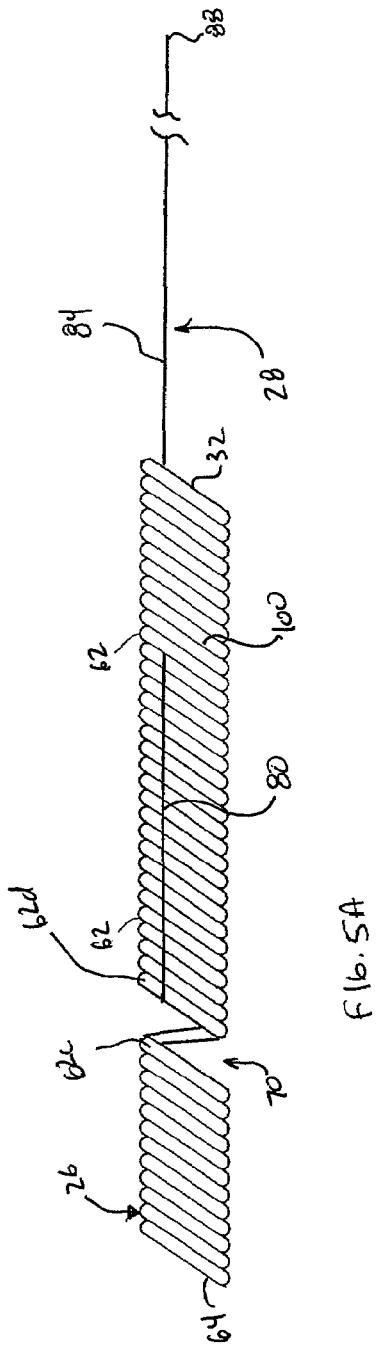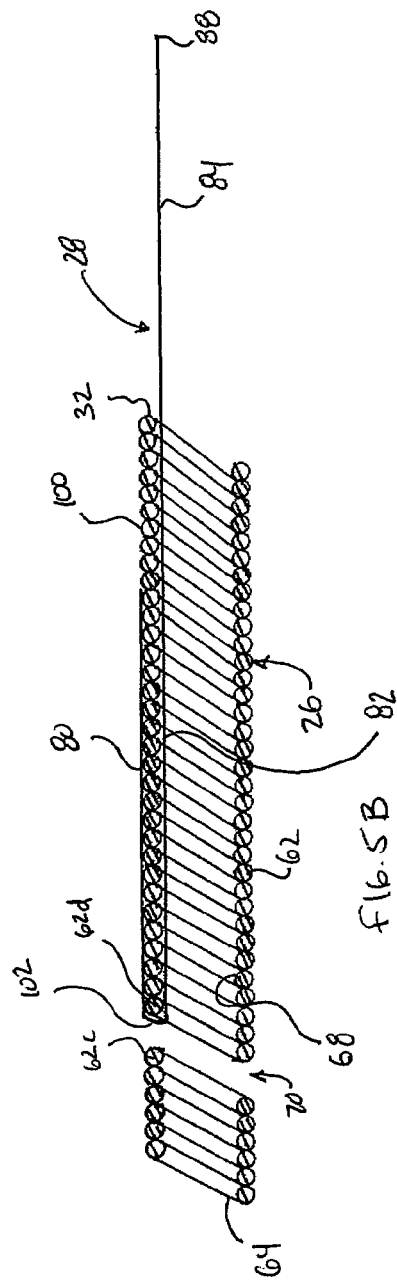

IMPLANTABLE MEDICAL LEAD ASSEMBLIES WITH DELIVERY TETHER

BACKGROUND

The present invention relates to implantable medical leads for connection between a stimulating control device and one or more stimulation or sensing electrodes and methods of manufacturing such leads, and more particularly to implantable leads and lead assemblies with coiled electrodes and means for implanting the same.

Systems and methods for electrical stimulation of electrically excitable tissue within the body of a living subject have been developed utilizing stimulating electrodes and a signal generator or control device to supply electrical charges in a controlled or predetermined manner. Such systems and methods have been developed specifically based upon a desired condition, such as to alleviate pain or to stimulate muscle movement, and based upon the application with a subject's body. For bodily applications where alleviation of pain is the goal, one or more stimulating and/or sensing electrodes can be implanted within nerve tissue, the brain or spinal cord for blocking pain sensation by electrical stimulation. For muscle tissue stimulation, a stimulating electrode can be implanted in a muscle tissue, whereby electrical current that is typically provided as pulses can cause muscle tissue reaction that may be controlled to cause movement of a subject's body part. Sensing electrodes are used for determining actions of the body.

Signal generators can determine when, how long, and/or the amperage of current pulses that are to be applied for the specific application, and often include hard-wired circuitry, a microprocessor with software and/or embedded logic as the controlling system for determining and dictating current pulses. Such signal generators may also be implanted within the subject's body, and typically such an implantation is done to position the signal generator close to the stimulating and/or sensing electrodes, with interconnecting medical leads for conducting current pulses to and from the stimulating and sensing electrodes. Implantable medical leads and externally utilized leads for these purposes are typically insulated conductors or conductive elements (e.g., a conductor disposed within a lead body), with conductive terminations at both ends for electrical connection with the signal generator and one or more electrodes. Implantable medical leads further have requirements for safe interbody use such as tissue compatibility, surgical procedure dynamics, and body fluid accommodation.

Signal generation and muscle tissue stimulation systems have more recently been envisioned for more complex control of a subject's bodily actions. One particularly complex muscular control concept has recently been considered for the purpose of re-teaching a subject how to swallow, the condition of inability to swallow being known as dysphagia. Techniques and methods of stimulating muscles within the neck region of a patient for the purposes of causing specifically determined muscles to react as a swallowing effect are described in PCT Publication No. WO 2004/028433, having a publication date of Apr. 8, 2004. Specifically, by implanting electrodes in two or more muscles of the upper airway musculature and connecting the electrodes with a signal generator that provides coordinated control signals, a swallowing action can be induced in the patient. Other specific techniques and methods are also disclosed in U.S. Pat. Nos. 5,725,564; 5,891,185; 5,987,359; 6,104,958; and 6,198,970; all to Freed et al. Other techniques and methods are disclosed in U.S. patent application Ser. No. 11/611,365, filed Dec. 15, 2006, and entitled "Method and Apparatus for Assisting Deglutition." The teachings of each of these references are incorporated herein by reference in their entireties.

For these and a variety of other implanted electrode stimulation treatments, conventional leads may not be optimal. For example, it may be difficult at best to achieve long term fixation of a medical lead's electrode at or against certain target tissue sites when employing conventional electrode configurations. Some muscles/muscle tissues are one such example whereby suturing or otherwise affixing a flat or ring-type electrode to the muscle's surface may not maintain a long term connection. Similarly, other target tissue sites are sensitive/fragile, or may require a more intimate contact with the electrode(s) to achieve the desired application of electrical impulses thereto via the electrode(s). Even further, muscles (as well as some other targeted tissue) will repeatedly move (e.g., contract) over time; the electrode used under these circumstances preferably exhibits some extensibility to accommodate these movements. Unfortunately, conventional flat or ring-type electrodes may not be able to satisfy these constraints.

To better meet the above needs (as well as possibly other needs) presented by some surgical sites, a coiled electrode can be employed. Coiled electrodes are generally known, can provide a form of self-fixation to the target tissue, ensure intimate contact with the tissue in question, and can be naturally extensible. For certain applications, it is desirable that the selected coiled electrode be soft or pliable so as to exhibit desired flexibility and/or minimize possible tissue damage. Coiled electrodes formed of platinum and iridium are an example of an acceptable coiled electrode material construction. With these and other similar coiled electrodes, the implantation technique generally entails mounting the coiled electrode to the conductor of the medical lead, delivering the medical lead to the target site, and then inserting the coiled electrode into the target tissue. As part of this insertion, a pulling force is applied to the distal end of the coiled electrode in piercing or otherwise inserting the coiled electrode into the target tissue. Due to the soft nature of many coiled electrodes, this pulling force can cause the coiled electrode to overtly stretch in a relatively inelastic manner, thus possibly damaging the coiled electrode.

In light of the above, a need exists for a coiled electrode lead assembly configuration promotes insertion of the coiled electrode into targeted tissue without overtly stretching the coiled electrode.

SUMMARY

Some aspects in accordance with the present disclosure relate to an implantable medical electrical lead assembly including a lead body, an elongated conductor, a coiled electrode, and a tether line. The lead body maintains the conductor. The coiled electrode, in turn, is coupled to the conductor, with this coupling resulting in the coiled electrode defining a proximal end and a distal end relative to extension from the conductor. The tether line defines a trailing segment and a leading segment terminating in a leading end. The tether line is coupled to the coiled electrode at a point proximal the distal end. Further, the leading end extends distal the distal end of the coiled electrode. With this configuration, a pulling force applied to the leading segment is transferred to the coiled electrode at a point proximal the distal end. During an implantation procedure, then, a pulling force applied to the tether line distal the coiled electrode is effectively transferred on to the coiled electrode as a pushing force, thereby minimizing an opportunity for overt stretching of the coiled electrode during implantation. In some embodiments, the lead assembly further includes a needle connected to the leading segment of the tether line that, in some embodiments, is a suture. In other embodiments, the coiled electrode defines a central passageway through which an intermediate segment of the tether line extends, with the distal segment extending distally along an exterior of the coiled electrode, and affixed thereto by adhesive.

Other aspects in accordance with the present disclosure relate to a method of making an implantable medical electrical lead assembly. The method includes providing a lead body maintaining an elongated conductor. A coiled electrode is also provided. The coiled electrode is coupled to the conductor so as to define a proximal end and a distal end. A tether line is provided, and defines a trailing segment and leading segment terminating at a leading end. The tether line is coupled to the coiled electrode at a point proximally spaced from the distal end. Further, the leading segment is extended from the coiled electrode such that the leading end is distal the distal end of the coiled electrode. In some embodiments, the method further includes coupling a needle to the leading segment of the tether line. In other embodiments, the method further includes providing the lead body as a having a side wall forming a lumen, with the coiled electrode being partially disposed within the lumen. With this approach, the method can further include applying an adhesive to bond the coiled electrode, the tether line and the side wall to one another in some embodiments.

Yet other aspects in accordance with the present disclosure relate to a method of implanting a medical lead. The method includes providing a medical lead assembly including a lead body maintaining an elongated conductor, a coiled electrode, a tether line, and a needle. The coiled electrode is coupled to the conductor. The tether line is coupled to the coiled electrode at a point proximal a distal end of the electrode, and a leading segment of the tether line extends distal the distal end. The needle is coupled to the leading segment. The lead body is then advanced toward a target site. Target tissue is pierced by the needle. A pulling force is applied to the needle to draw the coiled electrode into contact with the target tissue. In this regard, the pulling force is transferred by the tether line on to the coiled electrode at a point proximally spaced from the distal end of the coiled electrode. As a result, the pulling force is transferred into a pushing force as applied to the coiled electrode. The tether line is then severed, and the needle removed from the target site.

BRIEF DESCRIPTION OF THE DRAWINGS

FIG. 4 is an exploded side view of a tether line and a coiled electrode useful with the assembly of FIG. 1;

FIG. 5A is a side view of the tether line and coiled electrode of FIG. 4 upon final assembly;

FIG. 5B is a cross-sectional view of the assembly of FIG. 5A;

DETAILED DESCRIPTION

Figure 1:
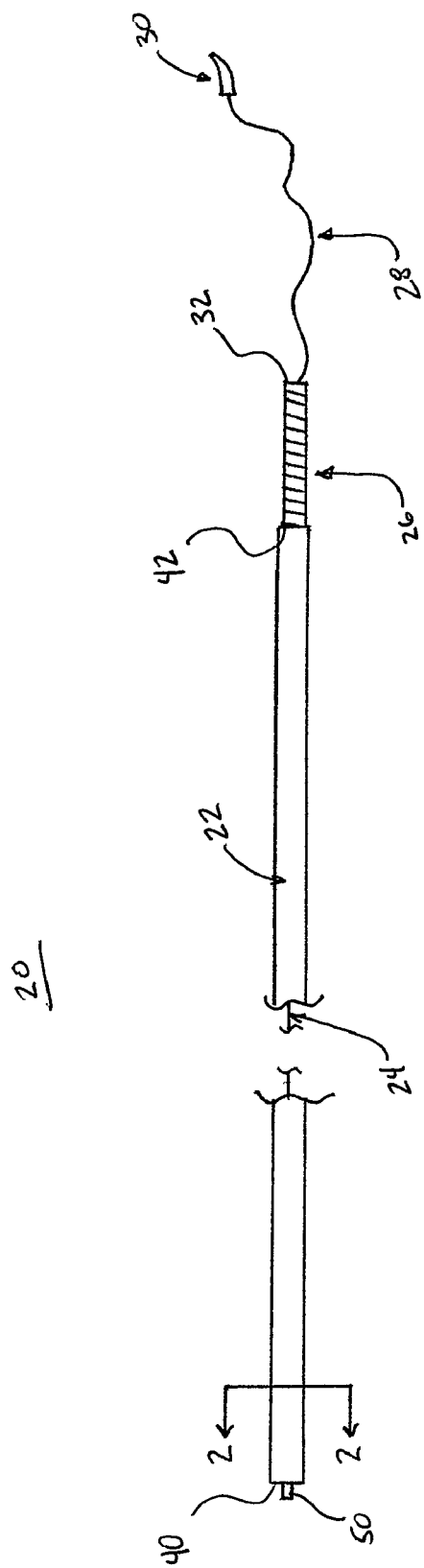
FIG. 1 is a side view of an implantable medical lead assembly in accordance with aspects of the present disclosure.

One embodiment of an implantable medical lead assembly 20 in accordance with aspects of the present disclosure is shown in FIG. 1. The lead assembly 20 includes a lead body 22, an elongated conductor 24, a coiled electrode 26, a tether line 28 and an optional needle 30. Details on the various components are provided below. In general terms, however, the conductor 24 is maintained by (e.g., electrically insulated) the lead body 22, and is coupled to the coiled electrode 26. The tether line 28 is also coupled to the coiled electrode 26, with a segment of the tether line 28 extending distal the electrode 26. In this regard, an initial point of coupling between the electrode 26 and the tether line 28 is proximal a distal end 32 of the electrode. Finally, where provided, the needle 30 is connected to the tether line 28 opposite the coiled electrode 26. With this configuration, a pulling force applied to the tether line 28, for example via a pulling force imparted upon the needle 30 during an implantation procedure, is transferred to the coiled electrode 26 proximal the distal end 32. Effectively, then, the pulling force is transferred to a pushing force upon the electrode 26, thereby reducing possible stretching of the coiled electrode 26 during implantation. Lead assemblies (or, more simply, leads) incorporating the above features can include additional components and/or provide desired characteristics appropriate for a particular end use application, and are implantable at a number of different bodily regions and to a variety of different target tissues.

The lead body 22 can assume a variety of forms as known in the implantable medical lead art, useful in electrically insulating the conductor 24. The lead body 22 can comprise any number of layers, which layers may be located directly on the conductor 24 or spaced from the conductor 24, and may include any number of functional layers. In some embodiments, the lead body 22 is formed of a silicone rubber material, although other materials selected to exhibit one or more properties desired for a particular implant application or procedure (e.g., softness, lubricity, etc.) are equally acceptable.

The lead body 22 can be described as extending between or defining a proximal side 40 and a distal side 42. While the lead body 22 is generally illustrated as having a continuous construction, in some embodiments the lead body 22 can be comprised of two or more sections having differing characteristics (either integrally formed, or separately provided and subsequently assembled). For example, the lead body 22 can have a decreased or decreasing diameter adjacent the distal side 42 as compared with a diameter adjacent the proximal side 40. With additional reference to FIG. 2, in some embodiments the lead body 22 is tubular, having a side wall 44 defining a lumen 46. As shown, the lumen 46 is sized to receive the conductor 24. Alternatively, portions of the lead body 22 can have a more solid construction (e.g., akin to a solid shaft) in maintaining the conductor 24 as described below. In connection with either of these constructions, however, the lead body 22 provides or forms the lumen 46 at or adjacent the distal side 42 for co-axially receiving the coiled electrode 26 as described below. In yet other embodiments, however, an entirety of the lead body 22 is solid and does not provide or form a discernable lumen. Finally, while the lead assembly 20 is depicted as including the single lead body 22, two or more of the lead bodies 22 can be provided and connected (e.g., bonded) to each other.

The conductor 24 can extend a substantial length of the lead body 22, forming or defining a proximal lead termination 50 that is electrically coupleable to one or more components of an implantable electrical stimulation and/or sensing system (e.g., lead extender, stimulation control unit or generator, etc.). A distal lead termination (hidden in FIG. 1) may also be formed, and is adapted for electrical coupling to the coiled electrode 26 as described below. In this regard, the conductor 24 can comprise any known or developed conductive wire or the like that may be a solid element (e.g., shaft, coil, etc.), and/or be comprised as a stranded conductor as such are well-known. Stranded wire as used for the conductor 24 would typically be more flexible as compared with solid wire. However, a solid wire is typically more capable of being deformed to hold a shape, and can exhibit a spring-back characteristic that may be useful with leads in accordance with some embodiments of the present disclosure. The lead termination 50 may be merely uninsulated wire portions for connection with other electrical connectors, or may comprise the connectors themselves as fixed to the end(s) of the conductor 26.

Figure 2:
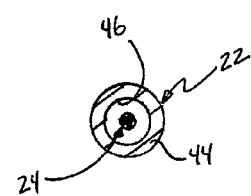
FIG. 2 is a cross-sectional view of a portion of the lead assembly of FIG. 1.

While FIGS. 1 and 2 reflects the single conductor 24 within the lead body 22, in other embodiments, two or more of the conductors 24 can be provided, and can be insulated from one another in a conventional manner (e.g., by insulation material coating). Further, while the lead body 22 is illustrated in FIG. 2 as forming or defining the continuous lumen 46, in other embodiments, the lumen 46 can be discontinuous, or the lead body 22 need not form or define the lumen 46. For example, the lead body 22 can encompass the conductor 26 within a material thickness of the lead body 22 (e.g., the lead body 22 can be molded to the conductor 26 that otherwise is provided in coil form, etc.).

Figure 3:
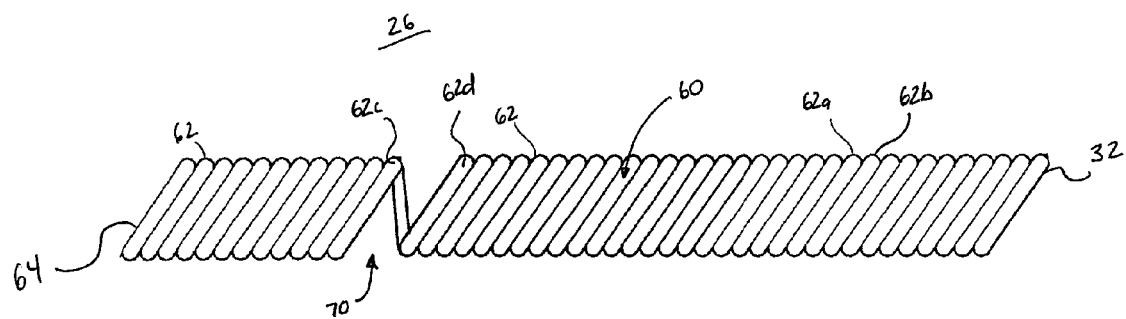
FIG. 3 is a side view of a coiled electrode useful with the assembly of FIG. 1.

With reference to FIGS. 1 and 3, the coiled electrode 26 can assume a variety of forms, and in some embodiments is formed of soft, surgically safe material. In one such embodiment, the coiled electrode 26 is a platinum iridium electrode. Regardless, the coiled electrode 26 can be a wire 60 (or a plurality of wires) wound to form a plurality of adjacent turns or coils 62 that combine to define a proximal end 64 (FIG. 3), the distal end 32, and a central passageway (hidden in the views of FIGS. 1 and 3, but shown at 68 in FIGS. 5A and 5B). The coiled electrode 26 can be tightly wound such that a majority of adjacent ones of the turns 62, such as the first and second turns 62a, 62b in FIG. 3, are arranged to be in contact with one another. For reasons made clear below, in some embodiments the coiled electrode 26 includes at least one pair of adjacent turns 60, such as the turns 62c, 62d in FIG. 3, that are not in contact with one another, thereby defining a gap 70. The gap 70 can be formed during the winding or coiling process in shaping the wire(s) 60 as the coiled electrode 26. Regardless, the gap 70 is positioned more closely adjacent the proximal end 64 than the distal end 32, and is sized to permit passage of the tether line 28 therethrough. In other embodiments, however, the turns 62 are uniform in relation to one another along an entire length of the coiled electrode 26 such that the gap 70 is not provided or is otherwise eliminated.

Returning to FIG. 1, the tether line 28 can assume a variety of forms, and is formed of a flexible material. For example, the tether line 28 can be a suture (e.g., silk suture, Prolene™ suture, braided suture, etc.), although other material(s) or constructions are also acceptable (e.g., thread, fiber, wire, etc.). Regardless, and with additional reference to FIG. 4 that otherwise illustrates the tether line 28 prior to assembly to the coiled electrode 26, the tether line 28 can be defined as having a trailing segment 80, an intermediate segment 82, and a leading segment 84. The trailing segment 80 terminates at a trailing end 86, whereas the leading segment 84 terminates at a leading end 88.

With the above designations in mind, the tether line 28 is assembled to the coiled electrode 26 such that the trailing segment 80 is coupled to the electrode 26 at a point proximal the distal end 32, and the leading segment 84 extends from the coiled electrode 26 such that the leading end 88 is distal the distal end 32 as shown in FIGS. 5A and 5B. More particularly, and in some embodiments, the tether line 28 passes through a portion of the central passageway 68, and is looped between an adjacent pair of the turns 62. For example, in one embodiment, the intermediate segment 82 extends within the central passageway 68 (best shown in FIG. 5B), and the trailing segment 80 is disposed along an exterior 100 (best shown in FIG. 5A) of the coiled electrode 26 and can be affixed thereto as described below. Conversely, the trailing segment 80 can be disposed within the central passageway 68, with the intermediate segment 82 being positioned along the exterior 100. Regardless, a transition 102 of the tether line 28 from the intermediate segment 82 to the trailing segment 80 passes or loops between an adjacent pair of the turns 62. In this manner, then tether line 28 effectively doubles back on itself over at least a partial length of the coiled electrode 26.

The above construction can be facilitated by provision of the gap 70. More particularly, the gap 70 provides a convenient location for passing of the tether line 28 between the adjacent turns 62c, 62d. In other embodiments, however, the gap 70 need not be provided. Even further, the tether line 28 need not be looped through the coiled electrode 26. Instead, the trailing segment 80, including the trailing end 86, can simply be affixed (e.g., bonded) to the coiled electrode 26 (either within the central passageway 68 or to the exterior 100) at a point proximally spaced from the distal end 32. With the one configuration above in which the tether line 28 is looped through the coiled electrode 26, however, the point at which the tether line 28 passes through the adjacent turns 62 (e.g., the turns 62c, 62d) effectively serves as the location point for transfer of a pulling force placed upon the tether line 28 to the coiled electrode 26. Thus, by proximally spacing the point at which the tether line 28 passes through the coiled electrode 26 from the distal end 32 thereof, the transferred force effectively serves to "push" the coiled electrode 26 distal the point of interface.

To promote a more complete affixment of the tether line 28 to the coiled electrode 26, an adhesive can be employed to bond the two components to one another. In this regard, and with additional reference to FIG. 6, the lead body 22 can be employed to effectuate a more complete connection. More particularly, and in some embodiments, the lumen 46 of the lead body 22 is sized to co-axially receive the coiled electrode 26, with a portion of the coiled electrode 26 extending distal the distal side 42 of the lead body 22. As shown, the coiled electrode 26/tether line 28 assembly is positioned related to the lead body 22 such that the trailing end 86 of the tether line 28 is adjacent the distal side 42 of the lead body 22 (or is not otherwise distally exposed relative to the distal side 42). Further, an adhesive 110 (referenced generally), such as a silicone adhesive, is disposed between the exterior 100 of the coiled electrode 26 and the side wall 44 of the lead body 22, and serves to affix or bond the tether line 28 relative to the coiled electrode 26 (as well as to the side wall 44 in some embodiments). The adhesive 110 can be positioned so as to subside at the distal side 42 of the lead body 22, as well as to encompass an entirety of the coiled electrode 26 within the lumen 46 (i.e., the portion of the coiled electrode 26 proximal the distal side 44).

Figure 6:
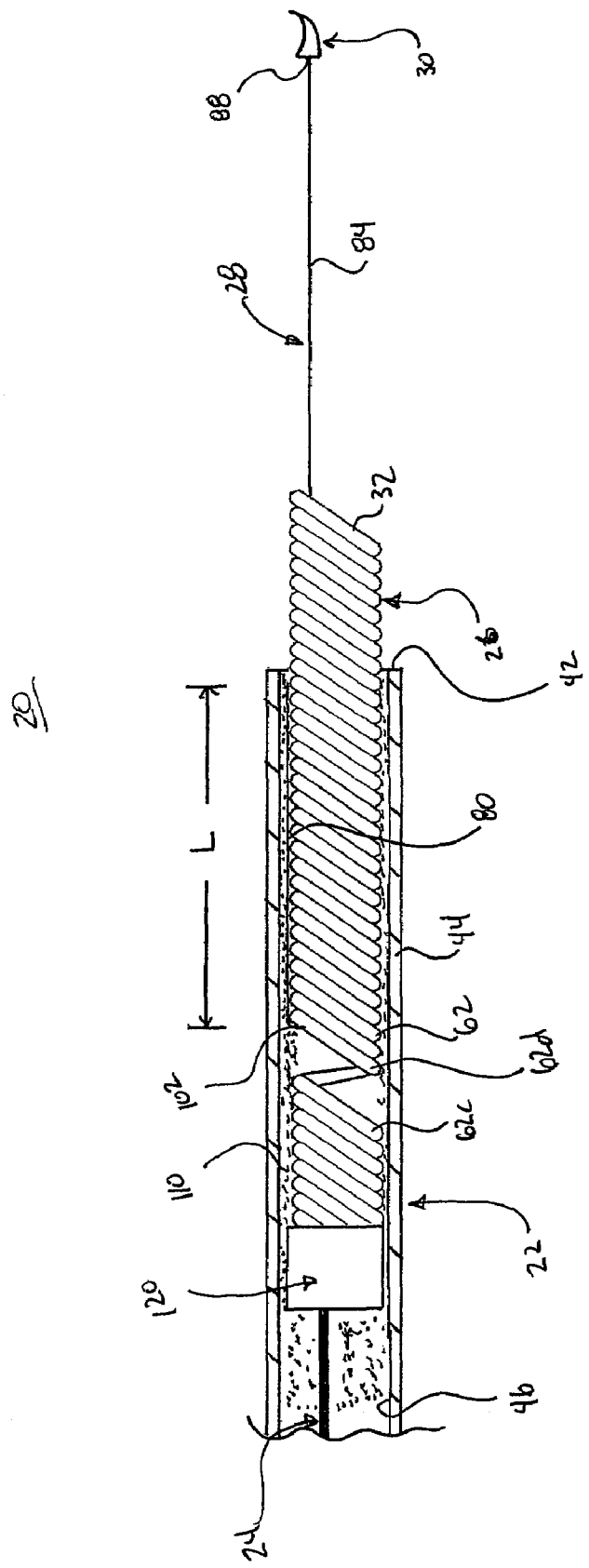
FIG. 6 is a partial cross-sectional view of a portion of the assembly of FIG. 1.

To further assist in maintaining the lead assembly 20 upon assembly, a crimp ring 120 can be provided as shown in FIG. 6. The crimp ring 120 can be disposed within the lumen 46, and serves to secure the conductor 24 to the proximal end 64 (hidden in FIG. 6, but shown in FIG. 3) of the coiled electrode 26. Where provided, the adhesive 110 can further be disposed to bond the crimp ring 120 to the conductor 24 as well as, in some embodiments, to the side wall 44 of the lead body 22. As a point of reference, the adhesive 110 can be dispensed relative to the crimp ring 120 by inserting a delivery needle (not shown) through the lead body 22 and into the lumen 46 immediately proximal the crimp ring 120, with the adhesive 110, in flowable or solution form, then being dispensed through the needle. Regardless, with embodiments in which the crimp ring 120 and the adhesive 110 are provided, the adhesive can be positioned to encompass a longitudinal length on the order of 0.2-1.0 inch proximal the crimp ring 120 to better ensure a robust connection. Alternatively, the crimp ring 120 and/or the adhesive 110 can be omitted and are not required components.

As reflected in FIG. 6, the trailing segment 80 of the tether line 28 defines a suture overlap length L relative to the coiled electrode 26 upon final assembly. It has been surprisingly found that where the overlap length L is not less than 0.2 inch, alternatively not less than 0.3 inch, and alternatively not less than 0.37 inch, the resultant assembly (in combination with adhesive bonding as described above) will maintain the affixment of the tether line 28 to the coiled electrode 26, and affixment of the coiled electrode 26 to the conductor 24 when the leading segment 84 of the tether line 28 is subjected to a pulling force of 0.50-lbf (i.e., a force applied to the leading segment 84 in a distal direction). Alternatively, the lead assembly 20 can exhibit other affixment characteristics that can exceed or be less than the 0.50-lbf pullout force parameter.

Finally, the needle 30, where provided, can be of any type known in the art, conventionally employed in piercing tissue, for example in delivering the coiled electrode 26 within target tissue. The needle 30 is coupled to the leading segment 84 of the tether line 28 (e.g., the leading end 88 is threaded through an opening of the needle 30 and tied), such that upon final assembly, the needle 30 is distal the distal end 32 of the coiled electrode 26.

Commensurate with the above, manufacture of the lead assembly 20 can include disposing the conductor 24 within the lead body 22, and coupling of the conductor 24 to the coiled electrode 26. The tether line 28 is passed within the central passageway 68 (FIG. 5B) of the coiled electrode 26, and looped between adjacent ones of the turns 62 at a point more closely adjacent the proximal end 64 (as compared to a location relative to the distal end 32). For example, the tether line 28 can be positioned such that the intermediate segment 82 (FIG. 5B) is within the central passageway 68 and the trailing segment 80 is along the exterior 100 of the coiled electrode 26. The tether line 28 is then affixed relative to the coiled electrode 26, such as by bonding the trailing segment 80 to the exterior 100 with the adhesive 110 as described above. In some embodiments, the adhesive 110 is not disposed within the central passageway 68 or does not otherwise effectuate bonding of the intermediate segment 82 to the coiled electrode 26 distal the point along the coiled electrode 26 at which the transition 102 passes between the adjacent turns 62 (e.g., the turns 62c, 62d). That is to say, while the trailing segment 80 can be bonded to the coiled electrode 26 distal the transition 102, the intermediate segment 82 is not; in this way, a pulling force applied to the leading segment 84 is transferred to, and imparted upon, the coiled electrode 26 at the transition 102. Were the intermediate segment 82 bonded to the coiled electrode 26 distal the transition 102, the distal most point of bonding between the intermediate segment 82 and the coiled electrode 26 would then serve as the point at which a pulling force applied to the leading segment 84 would be imparted upon the coiled electrode 26. It is desirable that the force transfer point be proximally spaced from the distal end 32 of the coiled electrode 26 as described above. In other embodiments, however, the intermediate segment 82 can be bonded or otherwise affixed to the coiled electrode 26 distal the transition 102.

Figure 7:
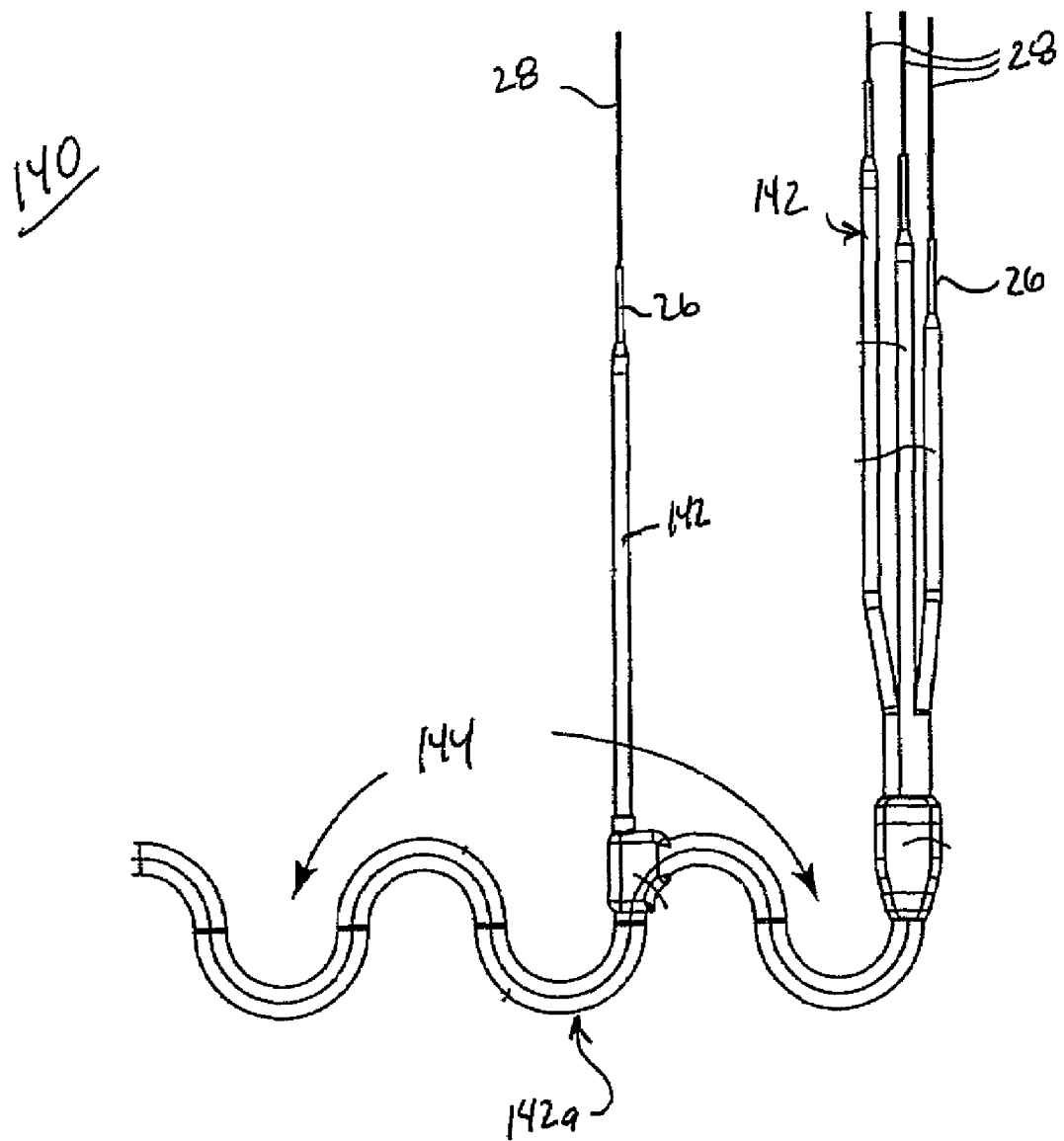
FIG. 7 is a side view of another embodiment lead assembly in accordance with aspects of the present disclosure.

In other embodiments, the lead assembly 20 can include additional features or components. For example, a cap having a distally tapering tip can be assembled over the coiled electrode 26 and associated with the distal side 42 of the lead body 22. Further, the lead assembly 20 can include one or more shaping features giving rise to enhanced flexibility and extensibility of the lead assembly 20 along a longitudinal length of the lead body 22 as described, for example, in U.S. application Ser. No. 11/413,316, filed Apr. 28, 2006 and entitled "Implantable Medical Leads and Lead Assemblies With Improved Flexibility and Extensibility To Facilitate Body Movements," the teachings of which are incorporated herein by reference. FIG. 7 illustrates one exemplary construction in accordance with this alternative embodiment, including a lead assembly 140 having a plurality of lead legs 142 at least one of which (e.g., the leg 142a) having a non-linear shape 144 (e.g., a sigmoid shape) that promotes longitudinal, elastic extension of the lead assembly 140.

Returning to FIGS. 1 and 5B, as part of an implantation procedure, the lead assembly 20 is provided as above, with the leading segment 84 of the tether line 28 (and the optional needle 30 assembled thereto) positioned or extending distal the distal end 32 of the coiled electrode 26. The lead body 22 is directed toward an implant target site (e.g., various bodily regions of a patient, such as a patient's neck, etc.). The needle 30 is manipulated by the surgeon to pierce through target tissue (e.g., muscle). A pulling force is applied to the needle 30 that in turn is transferred through the tether line 28 and on to the coiled electrode 26, sufficient to move the electrode 26 into contact with the target tissue. In this regard, the pulling force is focused upon the coiled electrode 26 at a point proximally spaced from the distal end 32. More particularly, the pulling force is transferred upon the point at which the transition 102 passes between adjacent turns 62, effectively transitioning the pulling force upon the needle 30 into a pushing force upon at least a majority of the coiled electrode 26. As a result, with continued pulling of the needle 30/tether line 28, the coiled electrode 26 is essentially pushed (i.e., that portion of the coiled electrode 26 distal the point at which the transition 102 passes between the adjacent turns 62 is "pushed") toward and into the target tissue.

Once the coiled electrode 26 has been desirably positioned or implanted within the target tissue, the tether line 28 is severed (e.g., at a point adjacent the distal end 32 of the coiled electrode 26), and the excess tether line 28 material and the needle 30 discarded. Once successfully implanted, the lead assembly 20 can be electrically connected to a stimulation generator (not shown) of a type known in the art, that can also be implanted within the patient at a point spaced from the implanted coiled electrode 26.

Although the present invention has been described with reference to preferred embodiments, workers skilled in the art will recognize that changes can be made in form and detail without departing from the spirit and scope of the present invention.

What is claimed is:

1. An implantable medical electrical lead assembly comprising:
a lead body maintaining an elongated conductor;
a coiled electrode coupled to the conductor and defining a proximal end and a distal end relative to extension from the conductor; and a tether line defining a trailing segment and a leading segment terminating at a leading end, wherein the tether line is coupled to the coiled electrode at a point proximally spaced from the distal end and the leading end extends distally from the distal end;

wherein a pulling force applied to the leading segment of the tether line is transferred to the coiled electrode at the point proximally spaced from the distal end.

2. The lead assembly of claim 1, further comprising:
a needle attached to the leading segment of the tether line.

3. The lead assembly of claim 1, wherein the tether line is looped through the coiled electrode.

4. The lead assembly of claim 1, wherein the tether line further defines an intermediate segment between the leading and trailing segments, and further wherein a transition of the intermediate segment to the trailing segment passes through adjacent turns of the coiled electrode.

5. The lead assembly of claim 4, wherein the coiled electrode defines a central passageway, and further wherein the intermediate segment extends within the central passageway and the trailing segment is disposed along an exterior of the coiled electrode.

6. The lead assembly of claim 5, wherein the trailing segment terminates at a trailing end, and further wherein the trailing end is bonded to the coiled electrode proximal the distal end.

7. The lead assembly of claim 4, wherein the coiled electrode includes a plurality of turns, and further wherein the plurality of turns forms a gap at which first and second adjacent turns are not in contact with one another, the transition passing through the gap.

8. The lead assembly of claim 7, wherein the gap is formed more closely adjacent the proximal end as compared to the distal end.

9. The lead assembly of claim 1, wherein the lead body includes a side wall forming a lumen along which a portion of the coiled electrode is disposed, the lead assembly further comprising:
adhesive bonding the tether line to the coiled electrode and the side wall.

10. The lead assembly of claim 9, wherein the lead body terminates at a distal side, and further wherein the adhesive is provided adjacent the distal side.

11. The lead assembly of claim 9, further comprising:
a crimp ring coupled to the proximal end of the coiled electrode and the conductor.

12. The lead assembly of claim 11, wherein the adhesive is provided along an entirety of a distal length of the lead body from the crimp ring to a distal side of the lead body.

13. The lead assembly of claim 1, wherein the trailing segment overlaps the coiled electrode over a length of not less than 0.37 inch.

14. The lead assembly of claim 1, wherein the tether line is a suture.

15. The lead assembly of claim 1, wherein the coiled electrode is formed of platinum and iridium.

16. A method of making an implantable medical electrical lead assembly, the method comprising:
providing a lead body maintaining an elongated conductor;
providing a coiled electrode;
coupling the coiled electrode to the conductor such that the coiled electrode defines a proximal end and a distal end;
providing a tether line defining a trailing segment and a leading segment terminating in a leading end;
coupling the tether line to the coiled electrode at a point proximally spaced from the distal end; and
extending the leading segment from the coiled electrode such that the leading end extends distally from the distal end.

17. The method of claim 16, further comprising:
connecting a needle to the leading segment.

18. The method of claim 16, wherein coupling the trailing segment to the coiled electrode includes threading the tether line between adjacent, first and second turns of the coiled electrode.

19. The method of claim 18, wherein the tether line further defines an intermediate segment between the trailing and leading segments, and further wherein coupling the trailing segment to the coiled electrode include positioning a transition of the tether line from the intermediate segment to the trailing segment between the first and second adjacent turns.

20. The method of claim 19, wherein the coiled electrode defines a central passageway, and further wherein coupling the trailing segment to the coiled electrode includes:
extending the intermediate segment through the central passageway; and
positioning the trailing segment along an exterior of the coiled electrode.

21. The method of claim 16, wherein coupling the trailing segment to the coiled electrode includes:
applying an adhesive to the trailing segment and the coiled electrode; and
bonding the trailing segment to the coiled electrode with the adhesive.

22. The method of claim 21, wherein the lead body includes a side wall forming a lumen, and further wherein:
coupling the coiled electrode to the conductor includes disposing a portion of the coiled electrode within the lumen; and
applying the adhesive includes dispensing the adhesive within the lumen.

23. The method of claim 22, further comprising:
attaching a crimp ring to the coiled electrode and the conductor.

24. The method of claim 16, wherein providing an electrode includes:
winding a wire to form a plurality of turns including first and second turns adjacent turns not in contact with one another to form a gap;
wherein the tether line is passed through the gap.

25. The method of claim 16, wherein providing a coiled electrode includes forming the coiled electrode from of platinum and iridium.

26. The method of claim 16, wherein the tether line is a suture.

27. A method of implanting an medical lead, the method comprising:
providing a medical lead assembly including:
a lead body maintaining an elongated conductor,
a coiled electrode coupled to the conductor and defining a proximal end and a distal end relative to extension from the conductor,
a tether line defining a trailing segment and a leading segment terminating at a leading end, wherein the tether line is coupled to the coiled electrode at a point proximally spaced from the distal end and the leading end extends distally from the distal end,
a needle coupled to the leading segment;
advancing the lead body toward a tissue target site;
piercing target tissue with the needle;
applying a pulling force on the needle to draw the coiled electrode into contact with the target tissue, wherein the pulling force is transferred by the tether line onto the coiled electrode at the point proximally spaced from the distal end for transferring the pulling force into a pushing force exerted upon at least a majority of the coiled electrode;

severing the tether line; and
removing the needle from the tissue target site.

* * * * *